US00PP18262P3

(12) United States Plant Patent
Parfitt et al.

(10) Patent No.: US PP18,262 P3
(45) Date of Patent: Dec. 4, 2007

(54) MALE PISTACHIO TREE NAMED 'RANDY'

(50) Latin Name: *Pistacia vera*
Varietal Denomination: Randy

(75) Inventors: Dan E. Parfitt, Davis, CA (US); Joseph Maranto, Bakersfield, CA (US); Craig E. Kallsen, Bakersfield, CA (US)

(73) Assignee: The Regents of the University of California, Oakland, CA (US)

( * ) Notice: Subject to any disclaimer, the term of this patent is extended or adjusted under 35 U.S.C. 154(b) by 210 days.

(21) Appl. No.: 11/085,894

(22) Filed: Mar. 21, 2005

(65) Prior Publication Data

US 2006/0212979 P1 Sep. 21, 2006

(51) Int. Cl.
*A01H 5/00* (2006.01)

(52) U.S. Cl. ..... Plt./152
(58) Field of Classification Search ..... Plt./152
See application file for complete search history.

(56) References Cited

PUBLICATIONS

U.S. Appl. No. 11/086,170, Parfitt et al.
U.S. Appl. No. 11/086,618, Parfitt et al.
Parfitt, D.E. et al. (1993) "Pistachio Cultivar Improvement: 1992," California Pistachio Industry, Annual Report, Crop Year 1992–93, p. 94.
Parfitt, D.E. et al. (1994) "Pistachio Cultivar Improvement: 1993," California Pistachio Industry, Annual Report, Crop Year 1993–94, pp. 98–99.
Parfitt, D.E. et al. (1995) "Pistachio Cultivar Improvement: 1994," California Pistachio Industry, Annual Report, Crop Year 1994–95, pp. 87–88.
Parfitt, D.E. et al. (1996) "Pistachio Cultivar Improvement: 1995," California Pistachio Industry, Annual Report, Crop Year 1995–96, pp. 90–98.
Parfitt, D.E. et al. (1997) "Pistachio Cultivar Improvement: 1996," California Pistachio Industry, Annual Report, Crop Year 1996–97, pp. 123–124.
Parfitt, D.E. et al. (1998) "Pistachio Cultivar Improvement: 1997," California Pistachio Industry, Annual Report, Crop Year 1997–98, pp. 134–142.
Parfitt, D.E. et al. (1999) "Pistachio Cultivar Improvement: 1998," California Pistachio Commission, 1998/99, Production Research Reports, pp. 230–279.
Parfitt, D.E. et al. (2000) "Pistachio Cultivar Improvement: 2000," California Pistachio Commission, 2000, Production Research Reports, pp. 303–304.
Parfitt, Dan E. et al. (1991) "Pistachio Cultivar Improvement – 1990," California Pistachio Industry, Annual Report, Crop Year 1990–91, pp. 118–119.
Parfitt, Dan E. et al. (1992) "Pistachio Cultivar Improvement – 1991," California Pistachio Industry, Annual Report, Crop Year 1991–92, pp. 163–164.
Parfitt, Dan E. et al. (1999) "Pistachio Cultivar Improvement: 1998," California Pistachio Industry, Annual Report, Crop Year 1998–1999, pp. 113–112.
Parfitt, Dan E. et al. (2000) "Pistachio Cultivar Improvement 1999," California Pistachio Industry, Annual Report, Crop Year 1999–2000, pp. 104–105.
Parfitt, Dan E. et al. (2001) "Pistachio Cultivar Improvement: 2000," California Pistachio Industry, Annual Report, Crop Year 2000–2001, pp. 141–142.

*Primary Examiner*—Kent Bell
*Assistant Examiner*—June Hwu
(74) *Attorney, Agent, or Firm*—Morrison & Foerster LLP

(57) ABSTRACT

A new and distinct variety of pistachio tree denominated 'Randy' is described. This cultivar is an early flowering male that will be used as a pollenizer for 'Golden Hills' and 'Lost Hills'. It has excellent flowering synchrony with 'Golden Hills' and 'Lost Hills' and can be used to cover the earlier part of the 'Kerman' flowering period during seasons in which 'Kerman' flowering is extended. This generally occurs during seasons of low chill, which are expected to become more frequent in the future due to continued global warming 'Peters', the standard male used to pollenize 'Kerman', often flowers too late to cover the earlier part of the 'Kerman' bloom period under these conditions. 'Randy' was selected for high pollen viability, durability, and a high level of pollen production (based on visual evaluation). 'Randy' flowers 2 to 4 weeks earlier than 'Peters', the standard pollenizer for 'Kerman'. 'Peters' flowers too late to be a very effective pollinator for the new cultivars.

11 Drawing Sheets

Botanical/commercial classification: (*Pistacia vera*)/new Pistachio variety.
Variety denomination: 'Randy'.

BACKGROUND OF THE INVENTION

The present invention relates to a new and distinct variety of Pistachio tree *Pistacia vera* which has been denominated varietally as 'Randy,' and more particularly to such a pistachio tree which has a flowering date of seven to ten days earlier than the industry standard pistachio tree variety 'Peters'.

'Randy' provides a good quantities of relatively durable and viable pollen. It has a good flowering overlap period with 'Golden Hills', described in U.S. Plant Pat. No. 17,158, 'Lost Hills', described in U.S. Plant Pat. No. 17,701, and 'Kerman' female cultivars and would be used as a pollenizer for these cultivars. 'Randy' is more precocious than 'Peters', flowering one or two years before 'Peters'. It would be advantageous to plant 'Randy' with 'Kerman' to provide adequate pollination for 'Kerman' trees newly coming into bearing and in situations of low chilling when 'Kerman' and 'Peters' may demonstrate poor synchrony for pollination.

SUMMARY OF THE INVENTION

It was found that the new cultivar exhibits the following combination of characteristics as compared to 'Peters', the industry standard: a) 'Randy' flowers 1 to 3 weeks earlier than 'Peters'; b) 'Randy' has significantly more buds per cm branch length and more spur branches than 'Peters', suggesting that 'Randy' produces many more male inflorescences per tree (and presumably more pollen) than 'Peters'; c) 'Randy' has more durable pollen than 'Peters'. The pollen stays viable for a longer period, which increases the effective amount of viable pollen available for pollination at any given time; d) Randy has appropriate flowering period overlap for 'Golden Hills' and 'Lost Hills'. 'Peters' flowers too late to serve as a pollenizer for these earlier flowering cultivars; and e) 'Randy' also has significantly larger buds than 'Peters'.

'Randy' has been asexually reproduced in Kern County, Calif. and Madera County, Calif. 'Randy' was propagated from buds, inserted into both PG-1 and UCB-1 rootstocks (budded onto). The cultivar is present at field Locations in Kern County, Calif. and Madera County, Calif. (test plots). In addition 2 trees have been budded on UCB-1 rootstocks in pots at Davis for planting into the field this spring.

DETAILED BOTANICAL DESCRIPTION

The following description describes the key characteristics of the new male pistachio cultivar named 'Randy' as well as references to the standard pistachio cultivar 'Peters' used as a pollenizer in California.

The cross: The cross that produced 'Randy' was made in 1990, and the progeny planted in 1991. The cross is between a *Pistacia vera* female '2-35', located in Kern County and propagated from buds supplied to Joseph Maranto from a plot at Davis in 1985, and a *Pistacia vera* male 'ES#3' originally from Chico, Calif. ES#3 is no longer available. This seedling was designated as B15-31. In 1997, a replicated yield trail was established near Lost Hills, Calif. In this plot, 'Randy' was budded onto either UCB-1 or PG-1 rootstock planted at the ends of alternate rows (alternating with 'Peters' male) between the female replicates. 'Randy' first flowered in 2000. A second replicated yield trail was established north of Fresno in September 1999. In this plot, 'Randy' is located at the ends of the rows, in alternate rows with 'Peters' and grafted to UCB-1 or PG-1 rootstocks. In this plot 'Randy' flowered in 2003. 'Randy' is stable and produces true to type in successive generations of asexual reproduction.

'Randy' may be distinguished from the female parent through examination of the flowers and flower buds, as all *Pistacia vera* are dioecious. Therefore all flowers in the 'Randy' inflorescence are staminate whereas the female parent, and all female pistachios have only pistillate flowers. Prior to annual flowering, 'Randy' may be distinguished from the female parent and all other female pistachios by examination of the flower buds, which are larger and more rounded than female flower buds. Randy buds are globular to conical whereas female inflorescence buds are cylindrical to ovate and distinctly pointed (obtuse) at the apical end of the buds. Male flower buds are generally larger than female flower buds.

Figure 7:
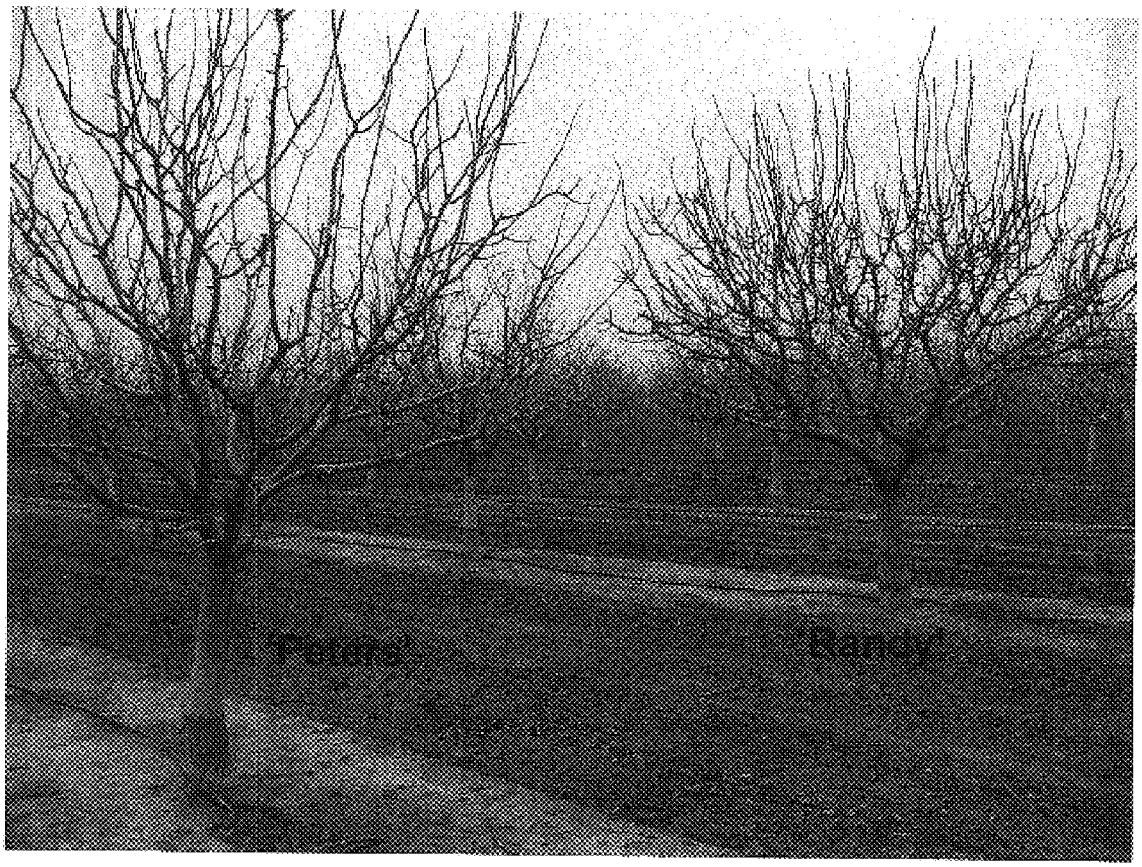
FIG. 7. Two 'Peters' trees flanking 'Randy' tree in center. Note larger tree size and large number of spur branches for 'Randy'.

Tree vigor: The tree is of average size for a pistachio, based on observation of 7 year old trees. Grafted trees are about 3 m tall at 7 years with a spread equal to the height. Trunk diameters are 10 to 15 cm, as measured at a trunk height of one meter. It is expected that 'Randy' will eventually be a larger tree than the female 'Kerman'. See FIGS. 4–5. 'Randy' is a significantly larger tree based on measured cross sectional area than 'Peters', although there may be some confounding rootstock effect for this character (ANOVA below). Close up photo evaluation of trunk lenticels was undertaken. Trunk lenticels were reddish-brown RHS138A,B to grey RHS201D in color. Trunk lenticels are two to four times wider than long and tend to become arranged in horizontal rows as trunk size increases. Trunk lenticel height ranged from 1.5 mm to 2 mm, width ranged from 2 mm to 5 mm. However, no obvious or significant differences in pattern, number, or appearance were seen between 'Randy' and 'Peters'. See Tables 1 and 2 and FIG. 7.

TABLE 1

ANOVA Table for xsec. area

| | DF | Sum of Squares | Mean Square | F-Value | P-Value | Lamb-da | Pow-er |
|---|---|---|---|---|---|---|---|
| Culti-var | 1 | 8413324.610 | 8413324.610 | 12.291 | .880 | 12.281 | .876 |
| Resi-dual | 5 | 5476071.158 | 884508.895 | | | | |

Means Table for xsec area
Effect: Cultivar

| | Count | Mean | Std. Dev. | Std. Err. |
|---|---|---|---|---|
| Peters | 5 | 3239.631 | 299.597 | 134.028 |
| Randy | 5 | 5074.114 | 1131.017 | 505.806 |

TABLE 2

| Fisher's PLSD for xsec. area<br>Effect: Cultivar<br>Significance Level: 5% | | | |
|---|---|---|---|
| | Mean Diff. | Crit. Diff. | P-Value |
| Peters, Randy | −1834.484 | 1208.645 | .0080 |

Figure 2A:
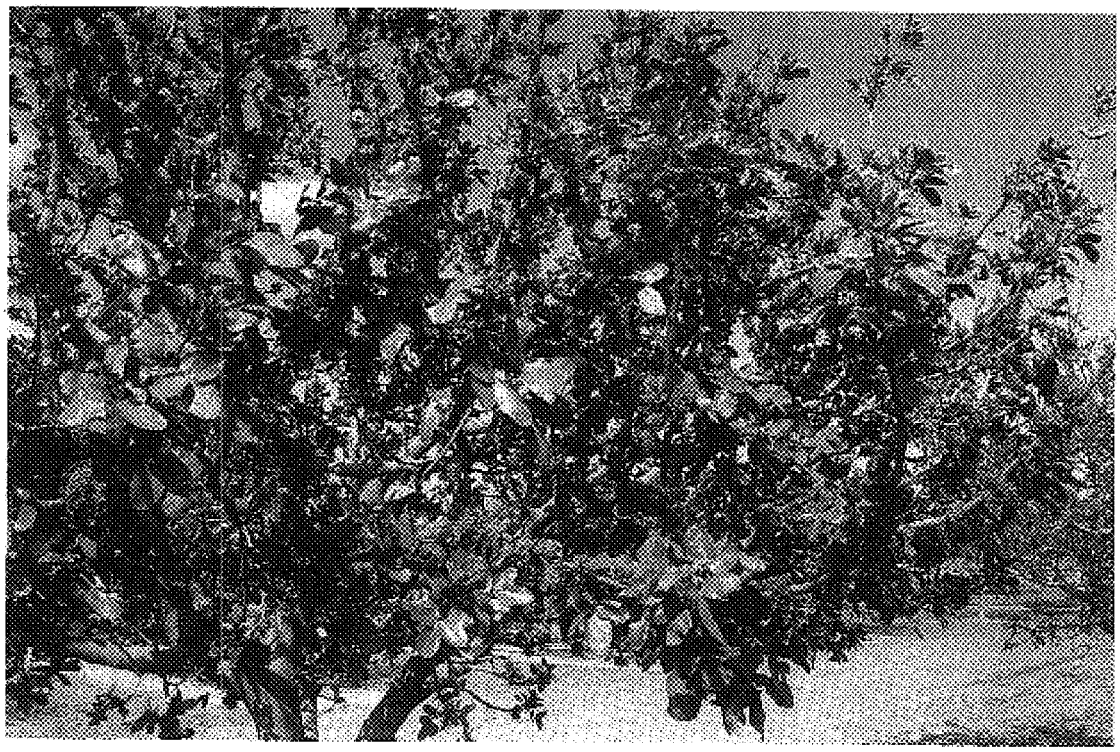
FIG. 2*a*. 'Randy' Inflorescences on Tree — 3/31/004
Figure 2B:
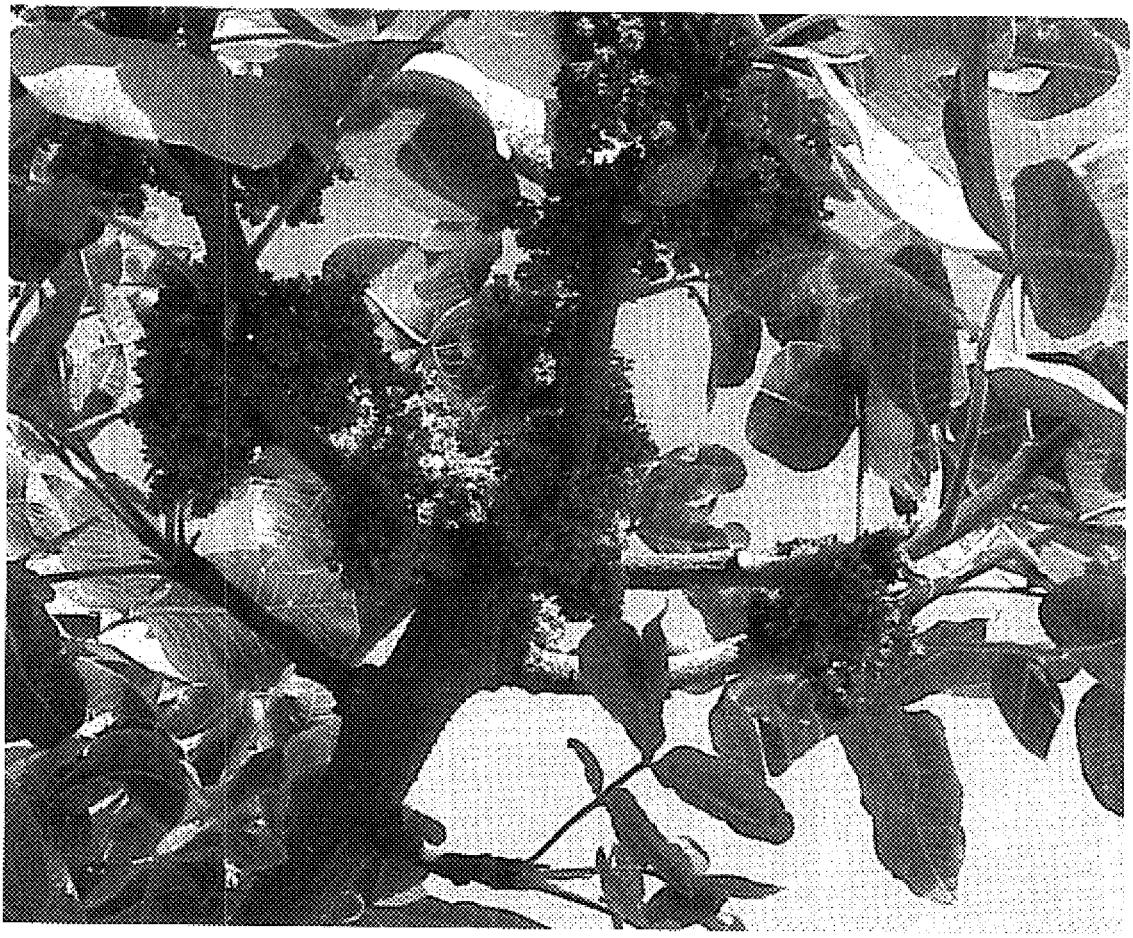
FIG. 2*b*. 'Randy' Inflorescences on Tree — 3/31/2004
Figure 4:
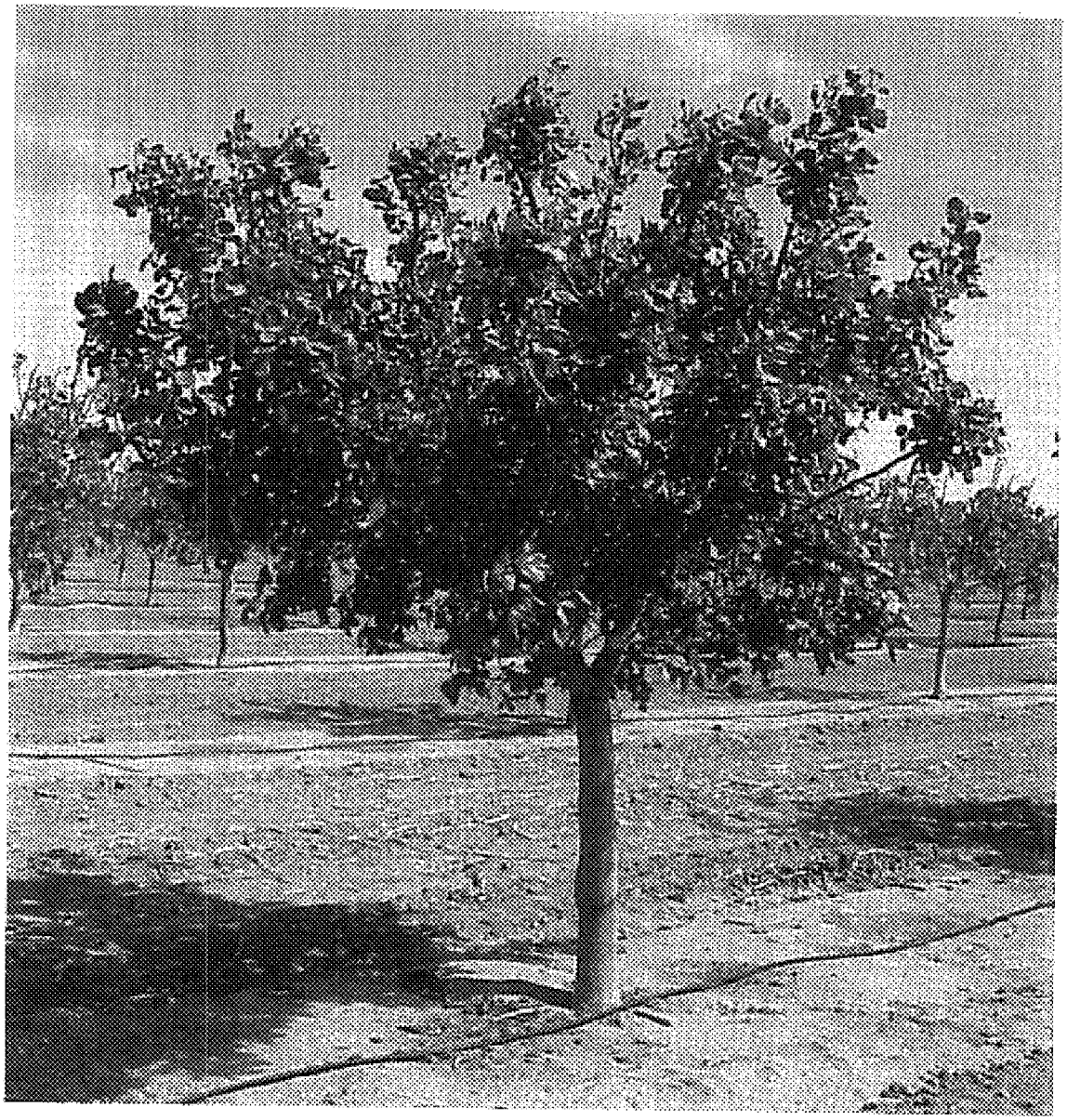
FIG. 4. 'Randy' tree taken on 4/11/02 at the Kern Co. test plot near Lost Hills.
Figure 5:
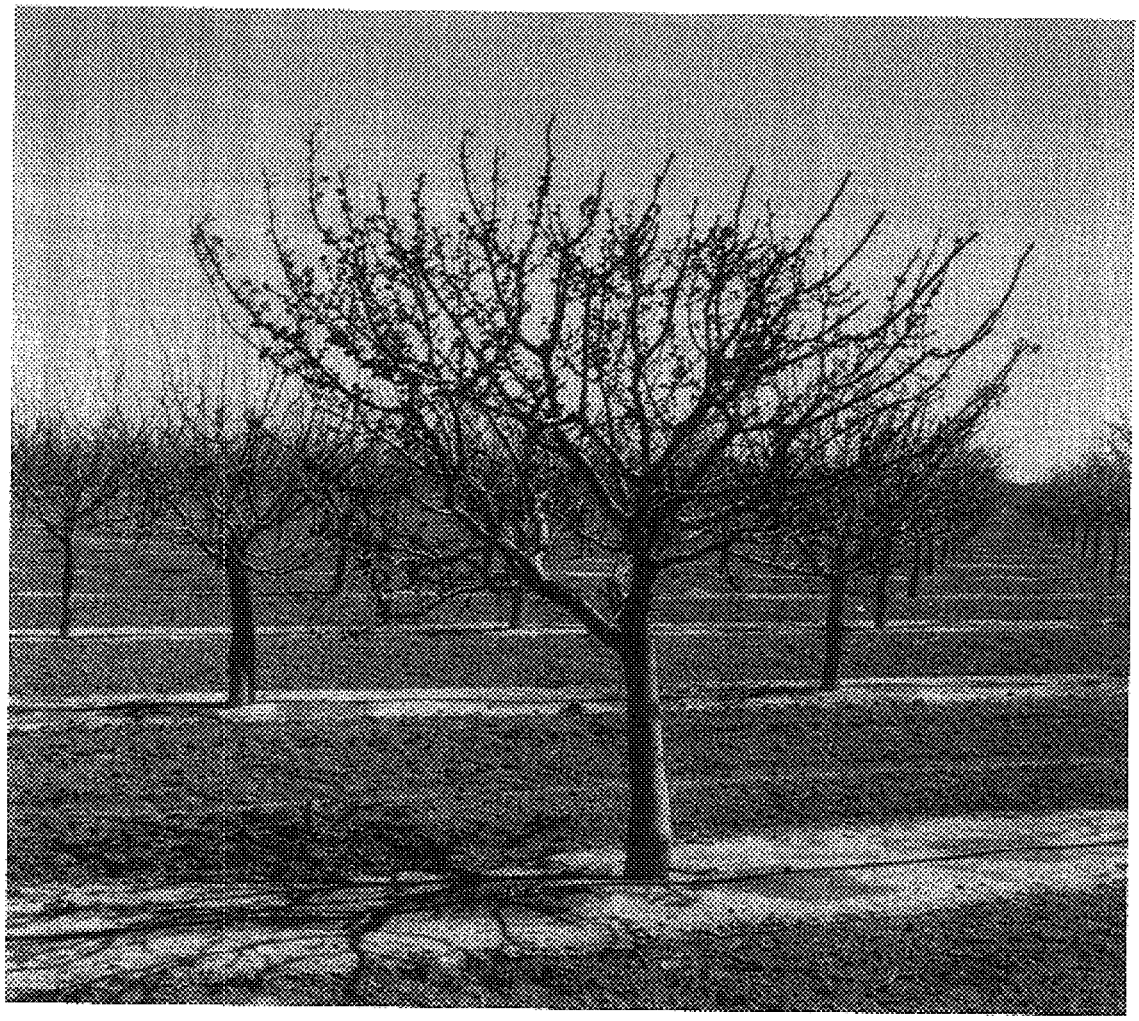
FIG. 5. 'Randy' at the Kern Co. advanced selection test plot, on 3/27/03.

Tree structure: 'Randy' has tree structure and branching habit typical for *Pistacia vera* L. (FIGS. 4 and 5). Branch angles are broad, ranging from 80 to 90 degrees for both scaffold and lateral branches (FIG. 2*b*). Distribution of scaffold and lateral branches is a function of pruning and training activities which are practiced intensively during the first three years of growth. Branch lenticels are grey RHS201D, scattered, oval to round, and one to two times wider than long. The branch lenticels are smaller than the trunk lenticels (width from 1–2 mm wide, height from <1 mm to 1 mm).

Flower buds: 'Randy' has significantly more buds per cm branch length than 'Peters'. 10 branches were measured on each of 5 trees of 'Randy' and 'Peters'. ANOVAs were run as a completely random design (observations not grouped by tree). See Tables 3 and 4.

TABLE 3

| ANOVA Table for buds/cm | | | | | | | |
|---|---|---|---|---|---|---|---|
| | DF | Sum of Squares | Mean Square | F-Value | P-Value | Lamb-da | Pow-er |
| Cultivar | 1 | 1.973 | 1.973 | 109.442 | <0001 | 109.442 | 1.000 |
| Residual | 98 | 1.787 | .018 | | | | |

| Means Table for buds/cm<br>Effect: Cultivar | | | | |
|---|---|---|---|---|
| | Count | Mean | Std. Dev. | Std. Err. |
| Peters | 50 | .187 | .124 | .018 |
| Randy | 50 | .468 | .144 | .020 |

TABLE 4

| Fisher's PLSD for buds/cm<br>Effect: Cultivar<br>Significance Level: 6% | | | |
|---|---|---|---|
| | Mean Diff. | Crit. Diff. | P-Value |
| Peters, Randy | −.281 | .053 | <0001 |

Figure 8A:
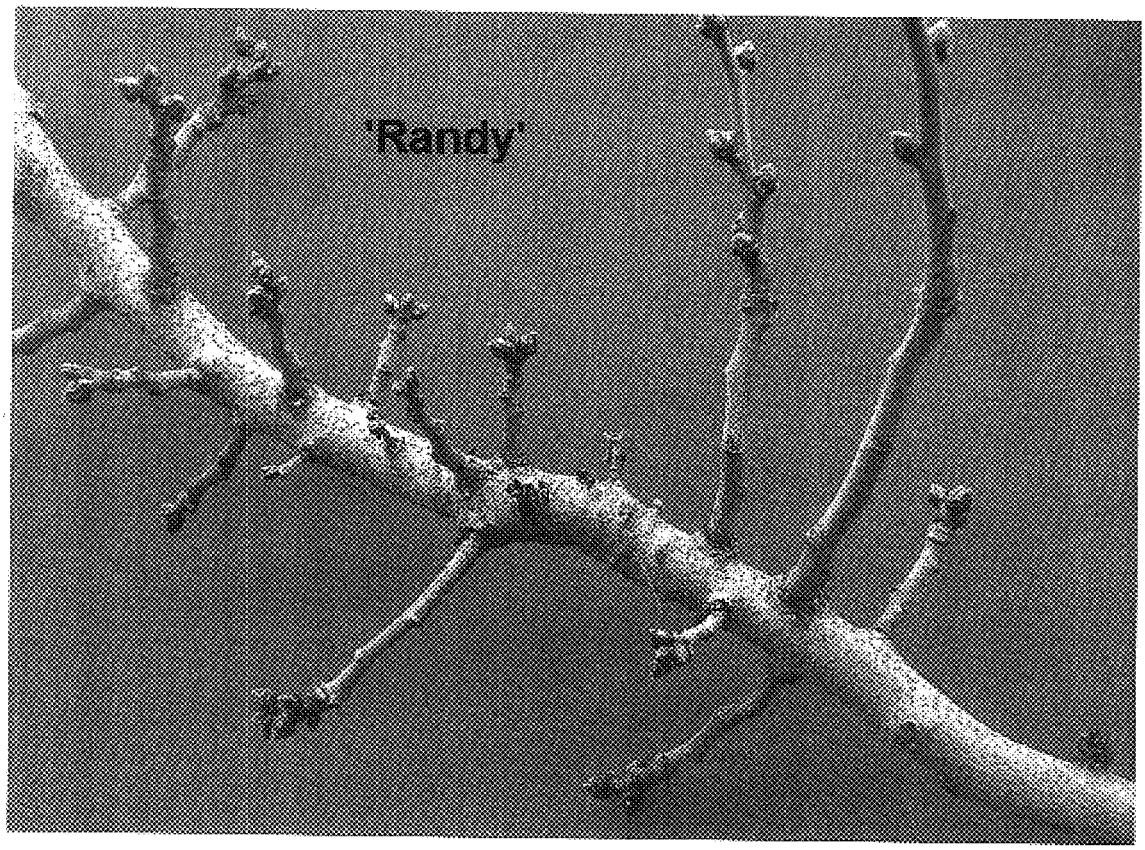
FIG. 8A. 'Randy' branch showing spurs.
Figure 8B:
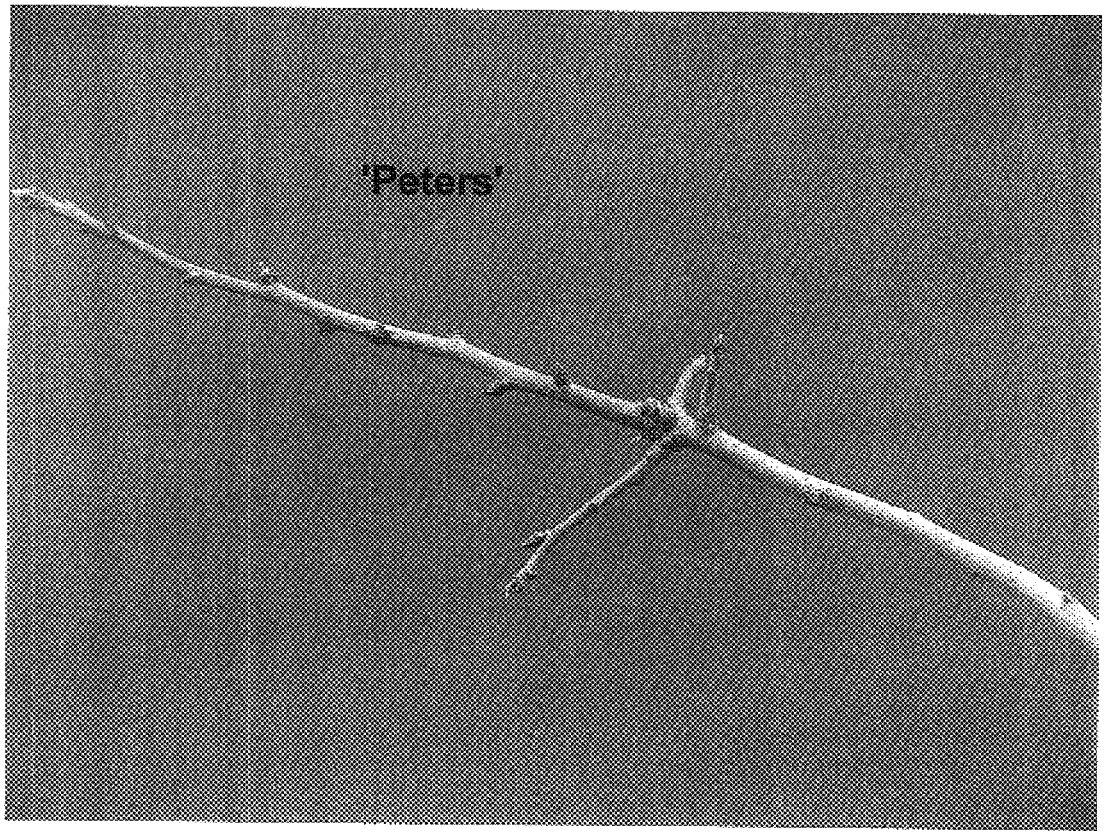
FIG. 8B. 'Peters' branch showing lack of spur branching.

'Randy' had more than twice as many buds per cm of flowering branch as 'Peters'. While this was not quantified, it was also observed that Randy has more spur branches than 'Peters'. See FIGS. 8A and 8B. This effect is quite pronounced, and diagnostic. The larger number of spur branches and buds/cm of branch means that 'Randy' produces many more male inflorescences per tree (and presumably more pollen) than 'Peters.'

'Randy' also has significantly larger buds than 'Peters'. 10 buds per tree were measured for width by length in mm. Length values for both sets of data were similar and non-significantly different, but 'Randy' buds were about 20% wider than 'Peters' buds, resulting in highly significant volume differences. See Tables 5 and 6.

TABLE 5

| ANOVA Table for bud vol (mm^3) | | | | | | | |
|---|---|---|---|---|---|---|---|
| | DF | Sum of Squares | Mean Square | F-Value | P-Value | Lamb-da | Pow-er |
| Cultivar | 1 | 171.185 | 171.185 | 57.565 | <.0801 | 57.565 | 1.000 |
| Resi-dual | 88 | 281.427 | 2.074 | | | | |

| ANOVA Table for bud I (mm) | | | | | | | |
|---|---|---|---|---|---|---|---|
| | DF | Sum of Squares | Mean Square | F-Value | P-Value | Lamb-da | Pow-er |
| Cultivar | 1 | .640 | .840 | .708 | .4023 | .708 | .127 |
| Resi-dual | 88 | 88.626 | .904 | | | | |

| ANOVA Table for bud w | | | | | | | |
|---|---|---|---|---|---|---|---|
| | DF | Sum of Squares | Mean Square | F-Value | P-Value | Lamb-da | Pow-er |
| Cultivar | 1 | 138.240 | 138.240 | 78.116 | <.0001 | 79.118 | 1.000 |
| Resi-dual | 88 | 172.476 | 1.760 | | | | |

| Means Table for bud vol (mm^3)<br>Effect: Cultivar | | | | |
|---|---|---|---|---|
| | Count | Mean | Std. Dev. | Std. Err. |
| Peters | 50 | 4.228 | 1.336 | .192 |
| Randy | 50 | 6.643 | 2.027 | .287 |

| Means Table for bud 1 (mm)<br>Effect: Cultivar | | | | |
|---|---|---|---|---|
| | Count | Mean | Std. Dev. | Std. Err. |
| Peters | 50 | 11.424 | .841 | .133 |
| Randy | 50 | 11.254 | .981 | .138 |

| Means Table for bud w<br>Effect: Cultivar | | | | |
|---|---|---|---|---|
| | Count | Mean | Std. Dev. | Std. Err. |
| Peters | 50 | 8.482 | 1.258 | .178 |
| Randy | 50 | 10.842 | 1.593 | .197 |

Figure 1:
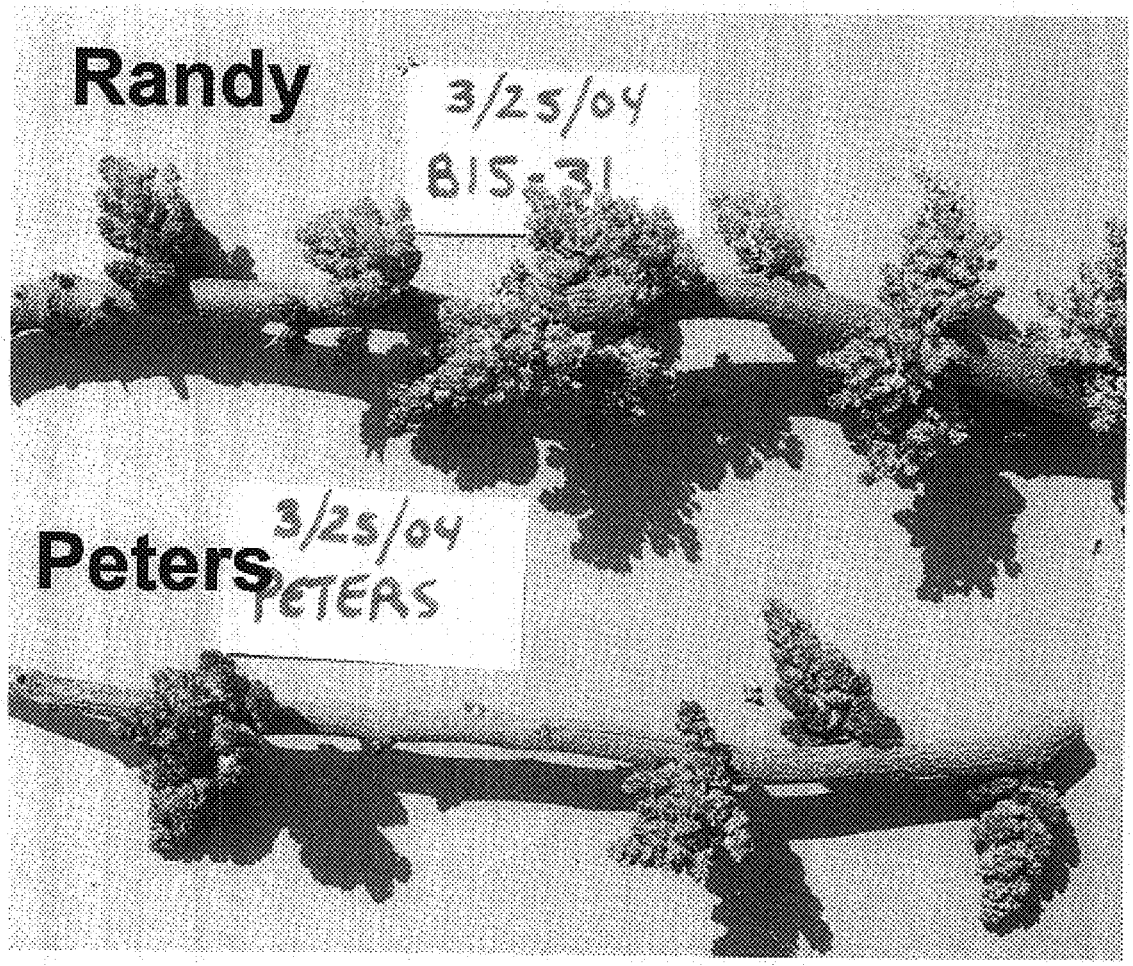
FIG. 1. Comparison photo of 'Randy' and 'Peters'
Figure 3A:
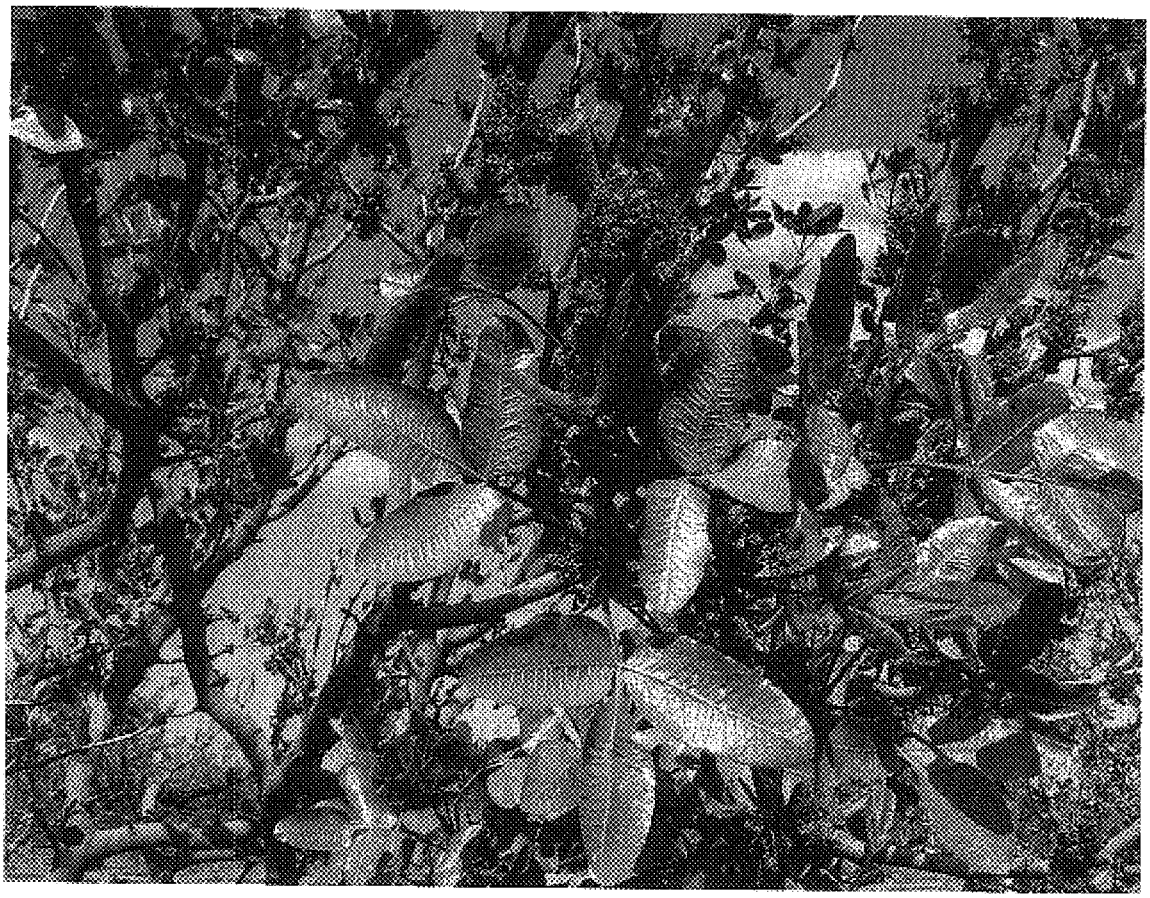
FIG. 3*a*. 'Peters' Inflorescences on Tree — 3/31/2004.
Figure 3B:
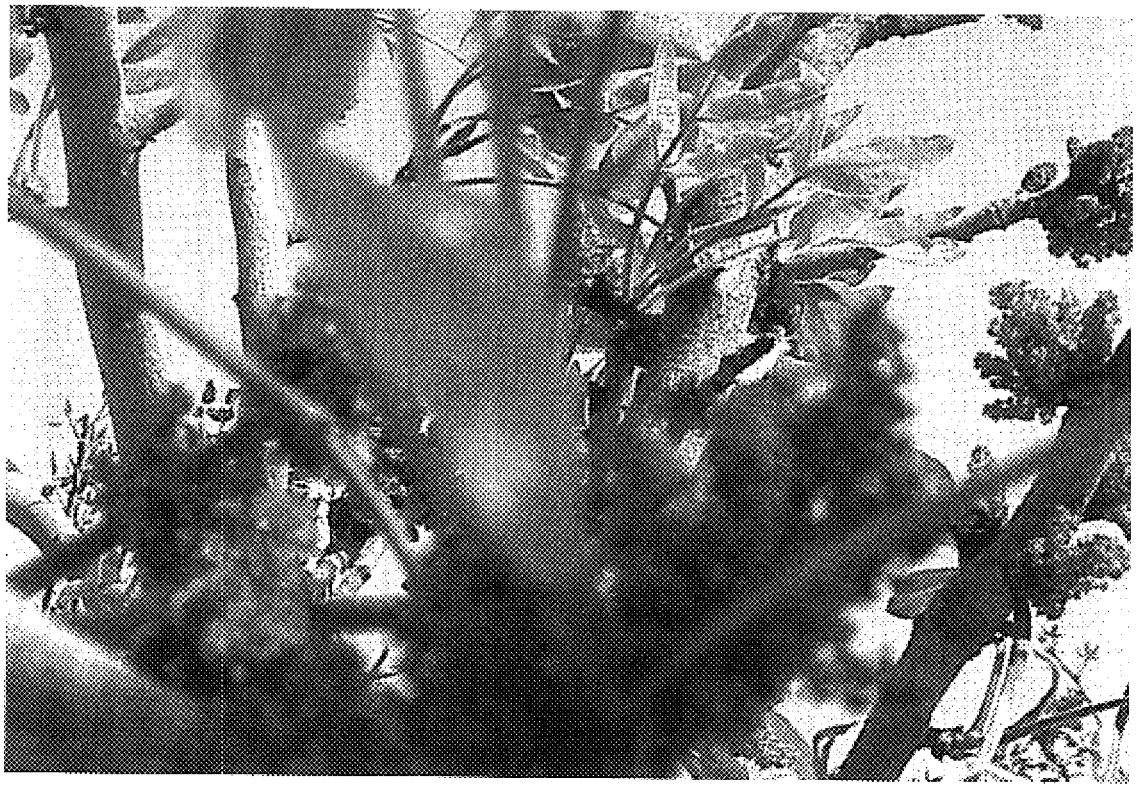
FIG. 3*b*. 'Peters' Inflorescences on Tree — 3/31/2004.
Figure 6:
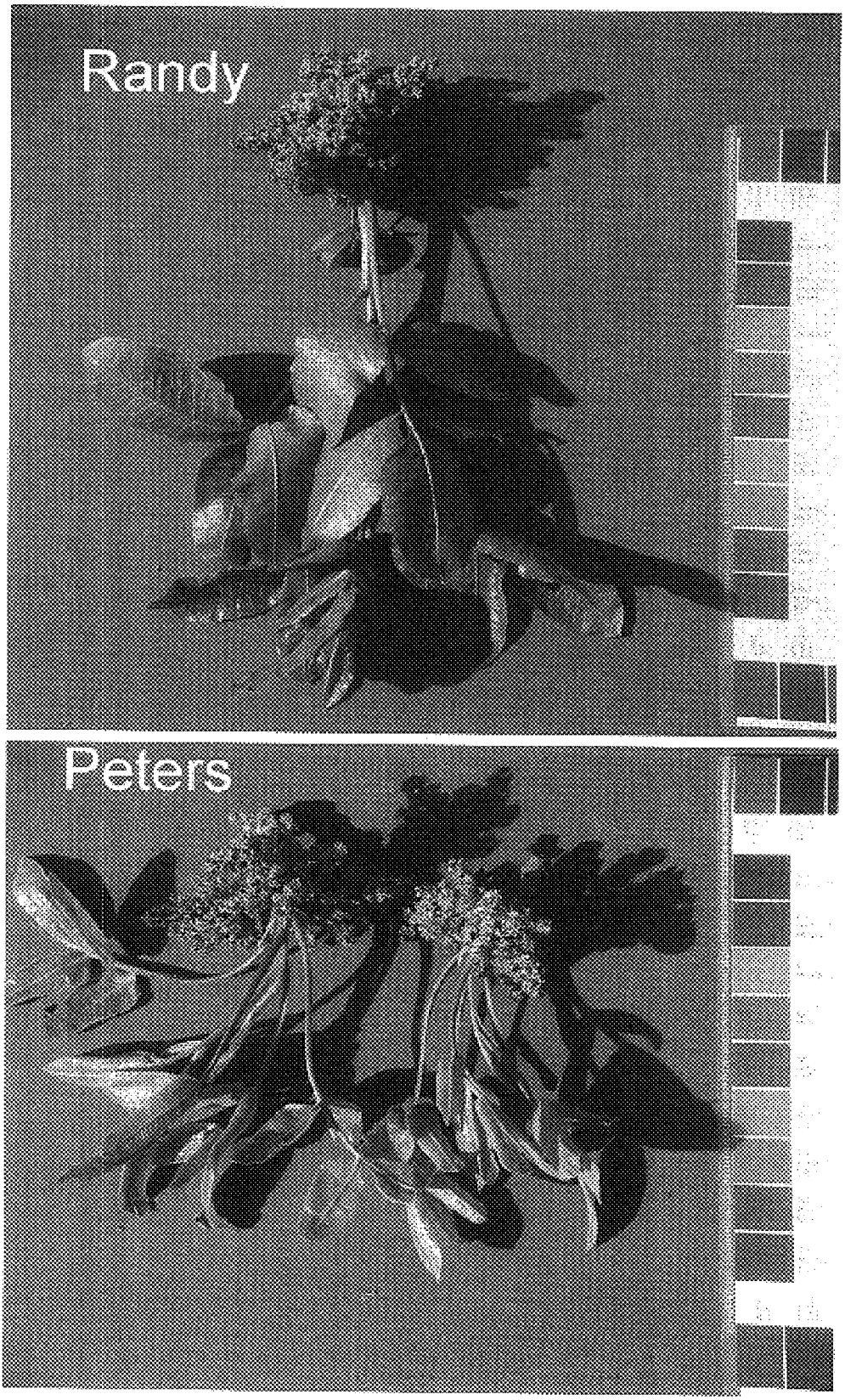
FIG. 6. Standardized comparison of 'Randy' and 'Peters' inflorescence and new leaves — 3/31/2004.

Inflorescences: Female inflorescences are born laterally alternately on branches, rarely as terminal buds. They are located on one year old wood. The flower buds form a branched compound inflorescence of the panicle form. Individual flowers are 0.5 mm to 1 mm in size. All flowers are male. The panicles are 3 to 7 cm long with considerable variation in size. Flower development is from base to tip of the panicle and typically spans a 3 week period, depending on weather conditions during individual seasons. Panicles are yellow as is the pollen. Tips of the panicles are tinged red prior to opening of individual flowers. FIGS. 1 and 6 show a comparison of 'Randy' vs. 'Peters' inflorescences. FIGS. 2*a* and *b* show 'Randy' inflorescences on the tree and FIGS. 3*a* and *b* show 'Peters' inflorescences on the same date (3/31/04). FIG. 6 shows a standardized comparison of 'Randy' and 'Peters' inflorescence and new leaves. Expanding 'Randy' inflorescences are red RHS52B, C to 54A (Red group) about 2 weeks prior to anthesis. At anthesis, flowers are yellow green RHS 145C to 154D (Yellow green group) trending to yellow RHS2D, 3D (Yellow group), many with a reddish pink tip where exposed to the sun RHS52A, 50A. This color may manifest in the folds of the anther lobes as well. 'Randy' flowers had 5 to 6 stamens per flower, 0.5 to 1 mm long at anthesis, with 4 lobed anthers, colors are as described above. Anthers are cylindrical (0.1–0.2 mm wide), tapering slightly to a blunt cuspidate to rounded tip.

Pollen viability: Pollen viability was measured with hanging drop slides in 1996. 'Randy' has highly viable and durable pollen. Initial readings (4/30/96) were 75% viable declining to 35% viable after 29 days of storage. 'Peters' initial viability was 45%, declining to 5% to 15% after 24 to 27 days. The pollen produced by appears to be more than that produced by 'Peters'.

Flowering date: 'Randy' flowers 1 to 3 weeks to earlier than 'Peters'. It is characterized by a relatively long bloom period, in excess of 2 weeks, a characteristic that 'Peters' shares. Most male pistachios have a flowering period of about one week. Peak flowering is a week earlier than for 'Kerman', approximately 2–3 days earlier than for 'Kerman' when sprayed with Volck supreme oil (470 wt) in 2003 and approximately one week earlier than 'Peters' depending on chilling hours. (Oil sprays are used to advance flowering by the industry and tend to compress the bloom period).

*Data from seedling test plot in Kern Co.*—1995: For 'Randy' — peak flowering 3/18/95 to 3/24/95 1996: For 'Randy' — 4/3/96 to 4/10/96; for 'Peters' — 4/23/96 to 5/3/96 1997: For 'Randy' — first flowering 3/24/97, peak flowering 4/1/97 to 4/4/97, last flowering 4/7/97 to 4/10/97 1998: For 'Randy' — first flowering 3/30/98-4/5/98, peak flowering 4/6/98-4/12/98, last flowering 4/13/98 to 4/20/98 1999: For 'Randy' — first flowering 3/8/99 to 3/12/99, peak flowering 3/15/99 to 3/19/99, last flowering 3/22/99 to 3/26/99 2000; For 'Randy' — first flowering 4/3/00 to 4/7/00

Data from grafted test plot in Kern Co. Trees were grafted on either 'UCB1' or 'Pioneer Gold 1' rootstocks. Visits to the two experimental sites were made at intervals of three to four days through the bloom period. In 2004 ($8^{th}$ year since grafting), a bloom-rating of 1 through 6 was used with 1=dormant; 2=early bloom, 3=mid bloom, 4=full bloom and 5=late bloom. Bloom evaluation is subjective; the number of individual flowers in bloom within an inflorescence varies, as does the degree of flowering at different locations along a branch. Full bloom was an estimate of when the maximum number of receptive stigmas was present on the tree. On Mar. 25, 2004, 'Randy' was past full bloom (4.5), 'Peters' was at early bloom (2.5).

Quantity of inflorescences: A visual score (low, medium, and high) was used to evaluate the 656 male seedlings at the Kern Co. seedling plot in 1997 and 1998. 'Randy' was scored as having a high number of inflorescences.

Leaves: Leaves are simple compound imparapinnate with 1 to 2 pairs of oppositely arranged leaflets. Leaves are 10 cm to 15 cm long with 5 cm to 8 cm leaflets. Leaves vary considerably in shape, in general being ovate with cuspidate to rounded tips and rounded base. Margins of leaf blades are entire. Leaf surfaces are glabrous, smooth and waxy. Leaflet upper and lower surfaces are the same in color, RHS138B, with the midrib vein RHS 145B, C in color. Petioles vary in color from RHS138A,B to RHS139C,D, with some having a tinge of purple-red RHS46A, near the base. Petioles are 2 to 4 cm long from the point of branch attachment to the basal leaflet. They are usually about 2/3 the length of the basal leaflet. They are shiny and glabrous with a few glands, somewhat angular in cross section but without wings.

Leafing date.— 1997: For 'Randy' — first leafing 4/7/97 to 4/10/97 1998: For 'Randy' — first leafing 4/13/98 to 4/20/98 1999: For 'Randy' — first leafing 3/15/99 to 3/19/99 2000: For 'Randy' — first leafing 4/3/00 to 4/7/00

'Randy' flowers earlier than 'Kerman' and, like 'Peters' has durable pollen. 'Randy' will be a superior pollenizer for the new female varieties 'Golden Hills' and 'Lost Hills' or any other variety which flowers up to 10 days earlier than Kerman. 'Randy' males would be useful in existing 'Kerman' orchards during seasons of low chilling or for other conditions when the flowering synchrony is poor, as 'Peters' is the tree that most often demonstrates flowering delay. 'Randy' grows quickly and is one to two years more precocious than 'Peters', which is a significant advantage in new orchards just coming into bearing.

Disease and pest traits: Pest and disease resistance in 'Randy' appear to be similar to 'Peters' (the standard Pistachio male cultivar), except that we did not observed as much 'Peters scorch', which is considered to be a physiological condition in which leaf margins turn dry and brown at the end of the growing season. 'Randy' is expected to be susceptible to *Verticullium* wilt (*V. dahliae*) if planted on its own roots, which is not done. No rootstock incompatibility was observed. *Botrysophaeria dothidea* and *Alternaria alternate* (pistachio shoot and leaf diseases) have not been evaluated since conditions were not favorable for disease development at the test plots.

Hardiness zone: In the test locations, 'Randy' has been exposed to low temperatures of −7 deg. C. and high temperatures of 46 deg. C. for at least 1 hour with no observable damage, −4 deg. C. to 44 deg. C. for at least 6 hours with no observable damage. Test plots for 'Randy ' are located in USDA hardiness zone 9a (20 deg. F. to 25 deg. F. low temperatures: −7 deg. C. to −4 deg. C.). Sunset Magazine® classifies *P. vera* in their climate zones 7–12, 14, 15, 18–21. Sunset zone 7 has typical winter lows of −13 deg. C. to −5 deg. C. Sunset zone 12 mean daily high temperatures are 38 deg. C. to 40 deg. C.

What we claim is:

1. A new and distinct variety of pistachio tree substantially as shown and described herein.

* * * * *